(12) United States Patent
Chappa et al.

(10) Patent No.: US 7,077,910 B2
(45) Date of Patent: Jul. 18, 2006

(54) LINEAR RAIL COATING APPARATUS AND METHOD

(75) Inventors: Ralph A. Chappa, Prior Lake, MN (US); Steven J. Porter, Minnetonka, MN (US)

(73) Assignee: SurModics, Inc., Eden Prairie, MN (US)

(*) Notice: Subject to any disclaimer, the term of this patent is extended or adjusted under 35 U.S.C. 154(b) by 6 days.

(21) Appl. No.: 10/409,434

(22) Filed: Apr. 7, 2003

(65) Prior Publication Data

US 2004/0194704 A1    Oct. 7, 2004

(51) Int. Cl.
B05C 11/02 (2006.01)
B05C 15/00 (2006.01)

(52) U.S. Cl. .............. 118/693; 118/663; 118/307; 118/319; 118/320; 606/194; 606/195

(58) Field of Classification Search ............... 118/500, 118/503, 319, 307, 320, 663, 693; 427/2.24, 427/2.28; 606/194, 195
See application file for complete search history.

(56) References Cited

U.S. PATENT DOCUMENTS

| | | | |
|---|---|---|---|
| 2,821,158 A | 1/1958 | Brown et al. | |
| 3,699,917 A | 10/1972 | Deverse et al. | |
| 3,936,549 A | 2/1976 | Kohler et al. | |
| 4,082,870 A | 4/1978 | Yenni | |
| 4,616,593 A | 10/1986 | Kawamura et al. | |
| 5,036,634 A * | 8/1991 | Lessard et al. | 52/79.1 |
| 5,049,404 A | 9/1991 | Kisler et al. | |
| 5,069,940 A | 12/1991 | Wenrick | |
| 5,207,343 A * | 5/1993 | Bogadi | 220/4.28 |
| 5,254,164 A | 10/1993 | Masahumi | |
| 5,421,979 A | 6/1995 | Stevenson | |
| 5,630,879 A | 5/1997 | Eichmann et al. | |
| 5,637,460 A | 6/1997 | Swan et al. | |
| 5,714,360 A | 2/1998 | Swan et al. | |
| 5,849,359 A | 12/1998 | Burns et al. | |
| 5,913,653 A | 6/1999 | Kempf | |
| 5,976,256 A | 11/1999 | Kawano | |
| 6,056,998 A | 5/2000 | Fujimoto | |
| 6,214,115 B1 | 4/2001 | Taylor et al. | |
| 6,562,136 B1 | 5/2003 | Chappa et al. | |
| 6,599,560 B1 * | 7/2003 | Daggett et al. | 427/9 |
| 6,743,462 B1 * | 6/2004 | Pacetti | 427/2.24 |
| 2002/0046521 A1 * | 4/2002 | Steinacker, Sr. | 52/274 |
| 2003/0003221 A1 | 1/2003 | Zhong et al. | |
| 2003/0059520 A1 | 3/2003 | Chen et al. | |

(Continued)

FOREIGN PATENT DOCUMENTS

FR    1304457    8/1962

(Continued)

Primary Examiner—George Koch
(74) Attorney, Agent, or Firm—Pauly, DeVries Smith & Deffner, LLC

(57) ABSTRACT

The invention provides an apparatus for coating a device comprising a coating chamber and a device rotator having at least one device mount wherein the apparatus allows insertion and retraction of the device on the device mount into and out of the coating chamber. In another aspect, the invention provides a method of applying a substantially uniform coating on a device comprising the steps of providing an apparatus for coating a device, mounting the device onto the device mount, purging the coating chamber to reduce humidity in the coating chamber, maintaining a reduced humidity content in the coating chamber, inserting the device into the coating chamber, disposing a coating material on the device and rotating the device mounts about the device axis.

20 Claims, 7 Drawing Sheets

U.S. PATENT DOCUMENTS

| | | | |
|---|---|---|---|
| 2003/0113439 A1* | 6/2003 | Pacetti et al. | 427/2.24 |
| 2003/0161937 A1* | 8/2003 | Leiby et al. | 427/2.24 |

FOREIGN PATENT DOCUMENTS

| | | |
|---|---|---|
| GB | 104464 | 3/1917 |
| GB | 525373 | 8/1940 |
| WO | WO 93/00174 | 1/1993 |
| WO | WO 99/55396 | 11/1999 |
| WO | WO 02/20174 A1 | 3/2002 |

\* cited by examiner

LINEAR RAIL COATING APPARATUS AND METHOD

FIELD OF THE INVENTION

The invention relates to a coating apparatus and method for applying a coating on a device. More specifically, the invention relates to an apparatus and method for providing a coating on a device having a surface geometry, such as a medical device. The apparatus and method provide for the coating of a device in an atmosphere-regulated environment.

BACKGROUND OF THE INVENTION

Medical devices are becoming increasingly complex in terms of function and geometry. Traditional coating methods, such as dip coating, are often undesirable for coating these complex geometries since coating solution may get entrapped in the device structure. This entrapped solution may cause webbing or bridging of the coating solution and may hinder the device function. Spray coating techniques have also been used to apply coatings to medical devices. However, current methods of spray coating have introduced operator error, and have resulted in reduced coating consistency and efficiency.

Therefore, a need remains for improved methods and apparatus for coating medical devices.

SUMMARY OF THE INVENTION

The invention provides an apparatus and method for applying a coating onto a device having surface geometry. The invention is particularly useful for coating medical devices, since such devices are often relatively small and can include complex surface configurations. The invention can be used to coat complex medical devices such as stents or other devices involving coils, coiled portions or cylinders having cut stent patterns.

An apparatus of the invention includes a device rotator having at least one device mount for retaining a medical device that is to be coated. The device mount is positioned on the device rotator, the device mount being rotatable around a device axis projecting outward from the device rotator. The apparatus also includes a coating chamber capable of accommodating a device on the device mount. The coating chamber includes a coating unit and an atmospheric maintenance system that can provide a coating to the device in low humidity. The apparatus can also allow for the movement of the device rotator, the coating chamber, or both, wherein the movement can allow the device on the device mount to be inserted into and retracted from the coating chamber.

In another embodiment, the apparatus includes a multi-device rotator having a plurality of device mounts projecting radially from the multi-device rotator, the device mounts being rotatable about a plurality of radial axes that project outward from a first axis.

The invention provides the ability to adjust or accommodate for complex surface geometries of the device, and to provide substantially uniform coatings. The invention also eliminates human factors in the coating system, and allows for increased throughput of coated devices. Further, the invention reduces wasted coating solution and reduces operator exposure to these coating solutions.

The invention also provides an apparatus that is easy to use. The device mounts, or portions thereof, can be removable, so that an operator can easily insert and remove the devices without disassembling the apparatus. The invention also eliminates variability in coating that can result from variations in positioning of the device on the holding apparatus.

The above summary of the present invention is not intended to describe each disclosed embodiment or every implementation of the present invention. The figures and the detailed description which follow more particularly exemplify these embodiments.

BRIEF DESCRIPTION OF THE DRAWINGS

The invention may be more completely understood in consideration of the following drawings of various embodiments of the invention, wherein like numerals represent like parts throughout the several views, in which.

Figure 1:
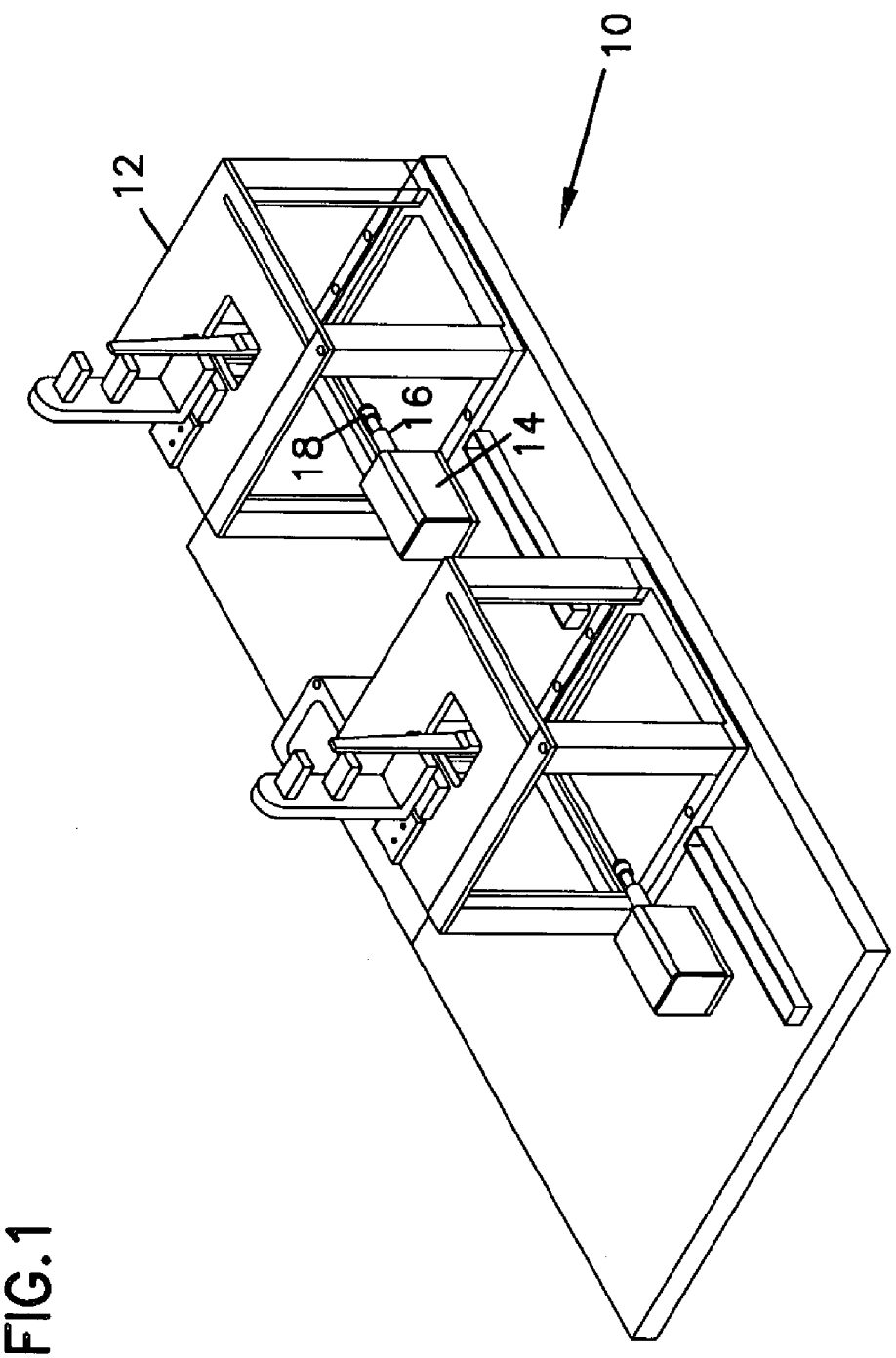
FIG. 1 is an illustration of a coating apparatus of the invention, including a device rotator and coating chamber.

While the invention is amenable to various modifications and alternative forms, specifics thereof have been shown by way of example in the drawings and will be described in detail. It should be understood, however, that the intention is not to limit the invention to the particular embodiments described.

DETAILED DESCRIPTION

Overview

The present invention relates to an apparatus for coating a device that includes a device rotator and coating chamber. The device rotator has at least one device mount positioned on the device rotator, the device mount being rotatable about a device axis. The coating chamber has at least one coating unit and an atmosphere maintenance system. The atmosphere maintenance system can monitor and regulate the humidity content within the coating chamber including during application of a coating material to the device. In an embodiment, the apparatus is arranged to allow the device mount to enter the coating chamber and to be positioned adjacent to the nozzle of the coating unit and within the spray path of the nozzle. The features of the coating apparatus, including the device rotator and the coating chamber, can allow for the application of a substantially uniform coating of a material, for example, a polymeric material, on a device, such as a medical device.

In one method of using the apparatus, a device is attached to the device rotator and is introduced into the coating chamber through a device aperture. Depending on the humidity in the coating chamber, the atmosphere maintenance system can be actuated to introduce gas and reduce humidity within the coating chamber and maintain a lowered level of humidity during the coating step. During the coating step the device is typically rotated about a device axis and moved perpendicular to the general direction of the spray path within the coating chamber while receiving an application of the coating compound.

The invention will be described generally with reference to FIG. 1. FIG. 1 depicts one embodiment of an apparatus for coating a device that is indicated generally as 10. In the embodiment shown in FIG. 1, the invention includes a coating chamber 12 and device rotator 14. Device rotator 14 includes a device mount 16 that projects outward from the device rotator 14 and towards the coating chamber 12. According to one method of the invention, devices are coupled with the device mounts 16 for application of a coating. The device rotator 14 is movable and can allow the device mount 16 to be inserted through device aperture 18 and into the coating chamber 12 and can bring the device mount 16 into the proximity of a portion of the coating unit. The atmosphere maintenance system is actuated to reduce and maintain the predetermined humidity levels within the coating chamber 12 as the device is coated.

The invention will now be described in more detail.

Coating Chamber

Figure 2:
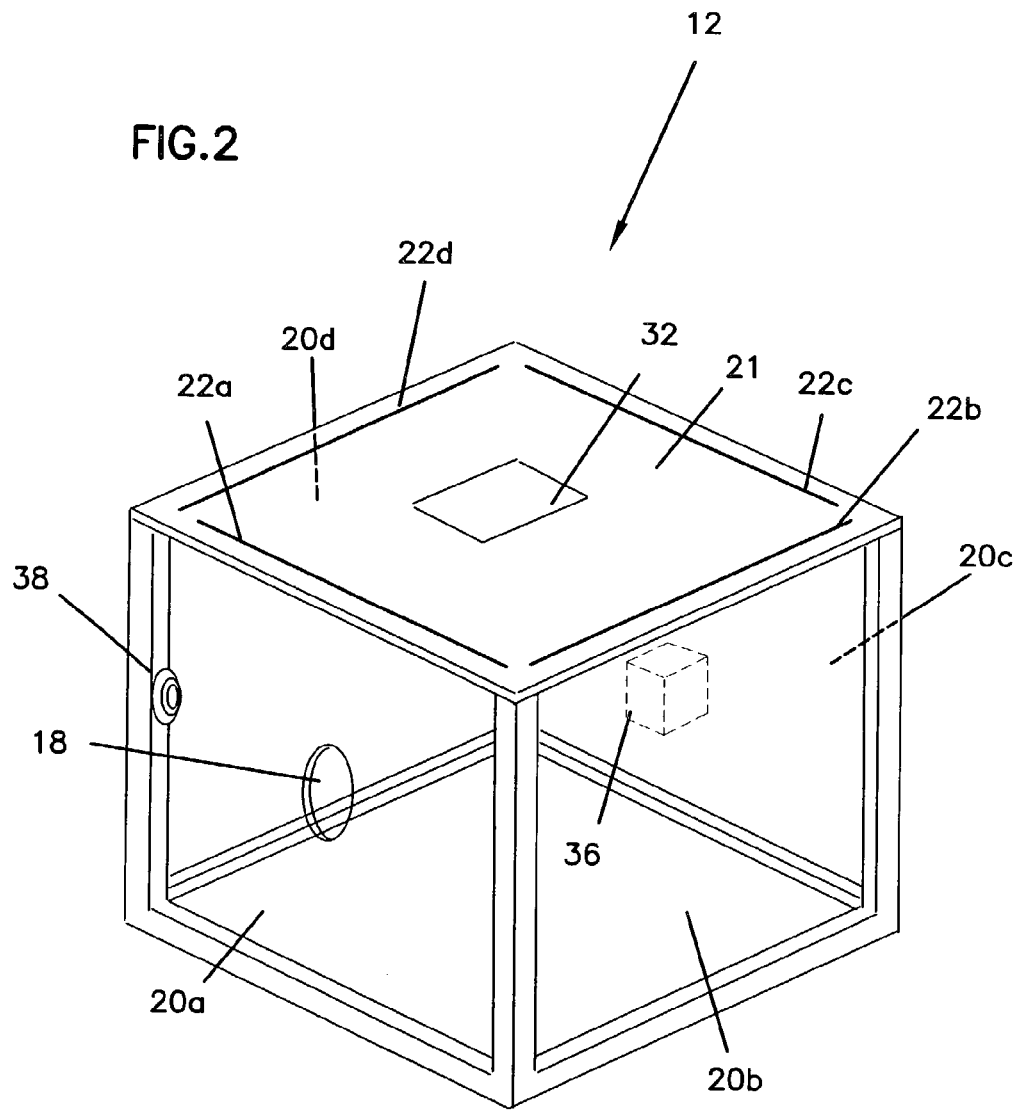
FIG. 2 illustrates a perspective view of the coating chamber of FIG. 1.

FIG. 2 illustrates one embodiment of the coating chamber 12 according to the invention. In this embodiment, coating chamber 12 includes a mounting panel 21, first panel 20a and third panel 20c, opposite each other; and second panel 20b and fourth panel 20d, opposite each other. Referring back to FIG. 1, coating chamber 12 is typically arranged on apparatus 10 with first panel 20a facing the device rotator 14. However, the coating apparatus 10 can be arranged with any panel having a device aperture 18 facing the device rotator 14. In other embodiments the coating chamber 12 can have more than one panel having a device aperture 18. This can be useful for the introduction of more than one device into the coating chamber simultaneously or independently.

In some embodiments, the mounting panel 21 also includes slots 22a–22d for the insertion and removal of first panel 20a, third panel 20c, second panel 20b, or fourth panel 20d. Panels can be removed and replaced from the coating chamber 12 when desired, for example, when the panels acquire an excessive amount of coating material or become damaged. The panels can be fabricated from plastic, for example, polypropylene, or glass, or any material suitable for use with the coating compounds applied within the chamber.

First panel 20a may also include device aperture 18 which can allow the passage of device mount 16 (shown in FIG. 1) and a device, when coupled to the device mount 16, into and out of the coating chamber 12. First panel 20a is fabricated out of a plastic material and device aperture 18 is created by boring, cutting, carving, or drilling a hole in the first panel 20a to a size that accommodates the device mount 16 (shown in FIG. 1) and the device introduced into the coating chamber 12. One advantageous aspect of the coating chamber 12 is that the first panel 20a can be readily removable and can be fabricated from a relatively inexpensive material (i.e., plastic). Therefore, a variety of different sized and shaped devices, or device holders, can be introduced into the coating chamber 12 and coated by simply changing the panel having the device aperture 18. In some cases, the size of the aperture is determined by the size of the device mount, the diameter of which can be larger than the diameter of the device itself. Coating chamber 12 can have more than one aperture, which can be used to introduce more than one device into the coating chamber 12.

The shape of the coating chamber typically includes flat sides and can be, for example, cubical, but other shapes are also contemplated. For example the coating chamber can include rounded or curved sides or panels. The coating chamber can be constructed in any shape to accommodate the particular device to be coated.

Coating Unit

Figure 3:
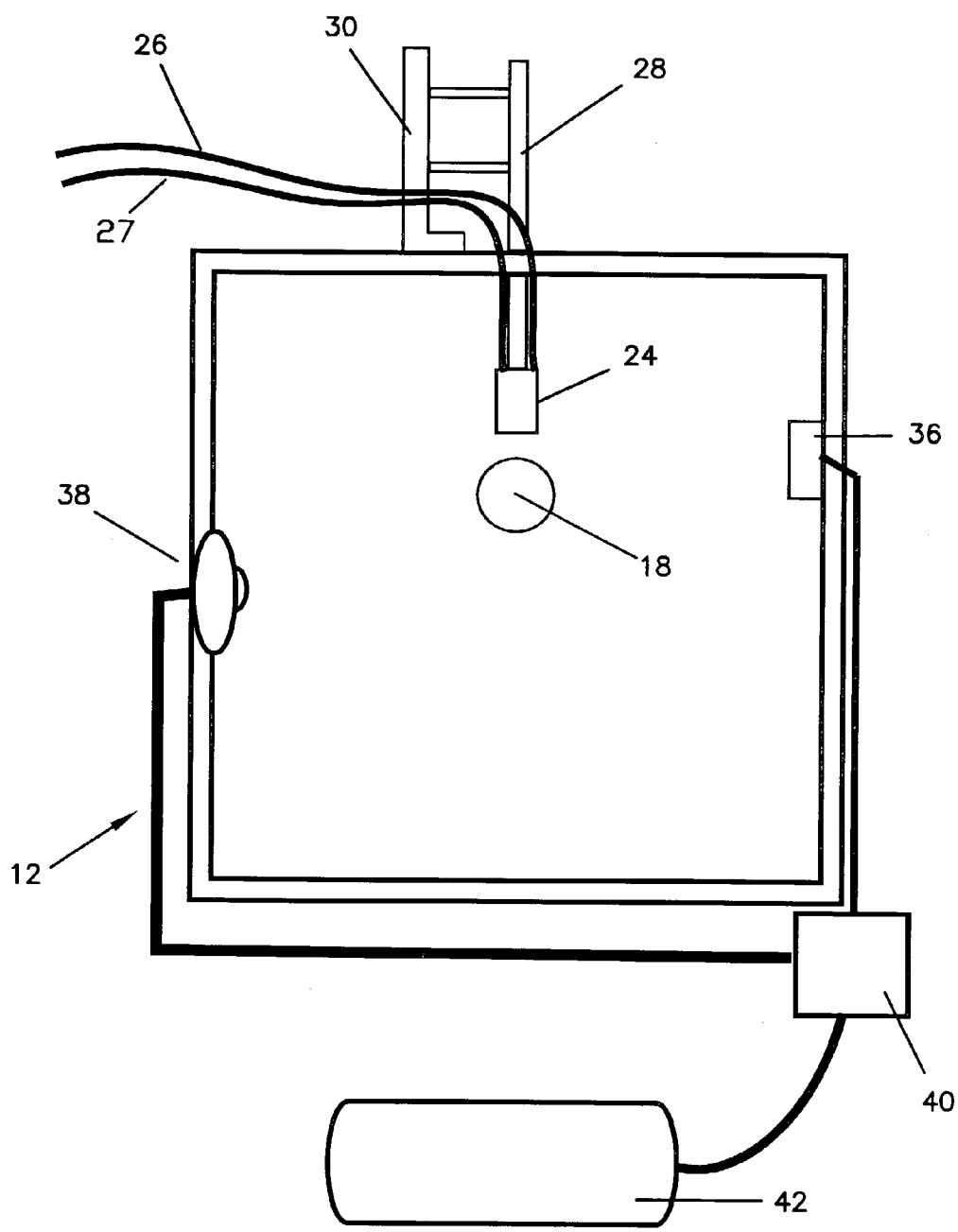
FIG. 3 illustrates a side view of an embodiment of the coating chamber of FIG. 1.

Coating chamber 12 includes a coating unit for the application of a coating material to the device. Referring to FIG. 3, coating unit includes nozzle 24, which is in fluid and gaseous connection with solution delivery line 26 and gas delivery line 27, respectively. The coating unit can also include nozzle arm 28 attached to positioning member 30. Positioning member 30 can be fastened to the mounting panel 21 and movable nozzle arm 28 passes through coating aperture 32 (referring to FIG. 2) into the interior of the coating chamber 12. The nozzle can be attached to a portion of the nozzle arm 28 to position the nozzle 24 within the coating chamber 12. However, positioning member 30 can be mounted on any portion of the coating chamber 12. In some embodiments, positioning member 30 is mounted on the outside of the coating chamber 12 on a panel. The positioning member 30 can be adjusted to change the location of the nozzle 24 in the coating chamber 12. Coating aperture 32 can be sealed with a piece of mylar or other material resistant to the compounds used in the process of the invention.

According to the invention and referring to FIG. 3, which presents a view of the coating chamber 12 from the perspective of the location of the device rotator 14, the nozzle 24 is adjacent to device aperture 18. This arrangement allows the device mount 16 (shown in FIG. 1) and device to be positioned adjacent to the nozzle 24 when the device is introduced into the coating chamber 12. The positioning member 30 can provide for the placement of the nozzle 24 adjacent to the device, when in the coating chamber 12. As used herein, "adjacent" means in sufficient proximity to allow application of a coating solution to a device mounted onto the device mount 16 and within the coating chamber 12, i.e., within the spray path of the nozzle 24. The position of the nozzle 24 in the coating chamber can be changed by adjusting the positioning member 30 to move the nozzle arm 28 in any direction. This distance can be adjusted depending upon such factors as the dimensions of the device to be coated and the distance desired between the device and the nozzle 24.

The solution delivery line 26 is typically connected to a pump and a reservoir (not shown) containing a solution of a compound to be coated on the device. A suitable pump can be obtained from IVEK Corporation (North Springfield, Vt.), for example the Digispense 2000 with RS 232 interface. The gas delivery line 27 is connected to a gas supply (not shown) that typically provides an inert gas. Operation of the coating unit typically involves supplying the coating solution and the gas to the nozzle 24 and will be described in more detail below.

Figure 4:
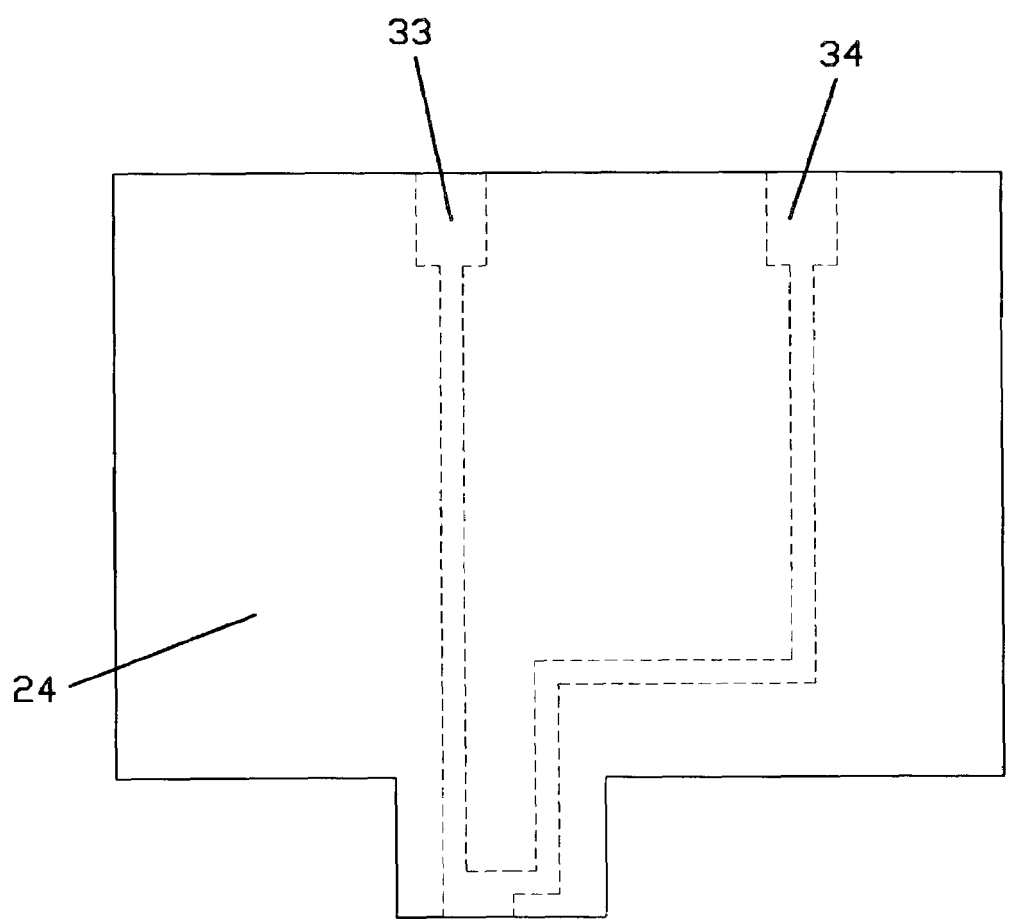
FIG. 4 illustrates a cross-sectional view of a nozzle of the apparatus.

FIG. 4 illustrates nozzle 24 according to the invention having a solution delivery channel 33 that can be connected to solution delivery line 26 (not shown). The nozzle 24 also includes a gas channel 34 that can be connected to gas delivery line 27 (not shown). The solution delivery channel 33 and gas delivery channel 34 can be provided as separate channels that are joined within the nozzle 24, so that the gas and solution are delivered from the nozzle 24 through a single opening. A suitable opening is approximately 0.040 inches (or about 1.016 mm) in some embodiments of the invention. The gas generally atomizes the coating solution. The gas is provided at sufficient pressure to provide good atomization of the coating solution. Different types of gases can be used. In many embodiments, the gas is inert, such as nitrogen. An example of a suitable nozzle is the Sonicair nozzle commercially available from Ivek Corporation (North Springfield, Vt.).

Atmosphere Maintenance System

Coating chamber 12 also includes an atmosphere maintenance system to control gas and vapor content within the coating chamber 12. It has been discovered that application of coating materials can be substantially improved by regulating gaseous conditions. The humidity level is one gaseous condition that is regulated in the coating chamber 12. Other gaseous conditions may also be regulated such as temperature. As shown in FIGS. 2 and 3, the atmosphere maintenance system includes humidity sensor 36 and gas inlet port 38. A suitable atmosphere maintenance system can be a closed loop control system and can be obtained from Proportion Air (McCordsville, Ind.), for example QB1T/QB2T with a relative humidity probe from Omega Engineering, Model No. HX94C (Stamford, Conn.). The gas inlet port can be, for example, a ¼" I.D. (interior diameter), ¼" NPT (National Pipe Taper) fitting (¼" is about 6.35 mm). According to the invention, humidity sensor 36 can measure the water vapor content in the interior of the coating chamber 12. Referring to FIG. 3, the humidity sensor 36 can be arranged to actuate a gas relay switch 40, or a comparable device, when the humidity levels within the chamber fall outside a predetermined range. Actuation of the gas relay switch 40 allows gas to flow from a gas supply source 42 to the gas inlet port 38 situated on the interior of the coating chamber 12. The gas supplied by the gas supply source 42 is generally nitrogen, helium, or clean refrigerated air. Although other gases may be used, non-explosive gases are desirable in most embodiments.

Generally, the distance between the humidity sensor 36 and the gas inlet port 38 is greater than the distance between the humidity sensor 36 and the nozzle 24. In the depicted embodiment, the humidity sensor 36 is positioned out of the spray path of the nozzle 24. Placing the humidity sensor 36 proximal to the nozzle 24 results in greater consistency and accuracy in the application of a coating compound to the device. It is thought that this proximal arrangement reflects a more accurate humidity measurement in the vicinity of the device when the device is being coated. The arrangement of these portions of the apparatus within the coating chamber 12 provides an improvement in the ability to obtain coatings that are more uniform and reproducible.

Size of Coating Chamber

In another aspect of the invention, it has been discovered that an appropriately sized coating chamber 12 can provide efficient reduction and stabilization of humidity. The coating chamber 12 is sized to allow rapid purging of water vapor (humidity) from the coating chamber 12 and maintenance of desired humidity levels during the coating cycle. In one embodiment, the volume of the interior of the coating chamber is not greater than about 2000 inches$^3$ (or about 32,774 cm$^3$. In another embodiment, the volume of the interior is in the range of 200 to 2000 inches$^3$ (or about 3,277 cm$^3$ to 32,774 cm$^3$). In still another embodiment, the interior of the chamber is not less than approximately 200 inches$^3$ (or about 3,277 cm$^3$). It has been discovered that if the interior of the coating chamber is too small, coating material can accumulate within the chamber and can interfere with other portions of the apparatus within the coating chamber 12, for example, the function of the gas inlet port 38 and the humidity sensor 36. Therefore, the coating chamber 12 is generally not less than approximately 200 inches$^3$ (or about 3,277 cm$^3$).

Coating Chamber—Other Aspects

In some embodiments, the coating chamber 12 can be arranged on the apparatus 10 to be movable in the direction of the device rotator 14. For example, the coating chamber 12 can be arranged on a slidable or rollable track to bring the coating chamber 12 towards the device rotator 14. The coating chamber 12 can be moved towards the device rotator 14 to introduce the device into the coating chamber 12 through device aperture 18. A drive unit (not shown) including a motor can control the movement of the coating station on the track.

Other features can be added to the coating chamber 12 or the apparatus 10 in general. In some embodiments the coating chamber 12 or apparatus 10 can include an illumination unit, for example, an ultraviolet light. Illumination units including a light-exposure device can be provided if a photoreactive coating is applied such as those described in U.S. Pat. No. 5,637,460 ("Restrained Multifunctional Reagent for Surface Modification," Swan et al.) and U.S. Pat. No. 5,714,360 ("Photoactivatable Water Soluble Cross-Linking Agents Containing an Onium Group," Swan et al.) (commonly assigned to the present Assignee, the disclosures of which are incorporated by reference). Also, one or more heating units can be provided if thermal curing of the coating is required. A motion-sensing unit can also be provided. The motion-sensing unit can employ infrared or visible light detectors for sensing movement and positioning of the device. Other motion-sensing units that can be used include radar detectors, for example, continuous wave radar systems. The positioning of the device or other movable portions of the apparatus can be determined in a sensor field and this information may be coupled with control circuitry that can, for example, actuate function of a motor that drives the movement of the device rotator and the device in a particular direction. The control circuitry may include a microprocessor to control the actuator based on these multiple pieces of information.

Device Rotator

Figure 5:
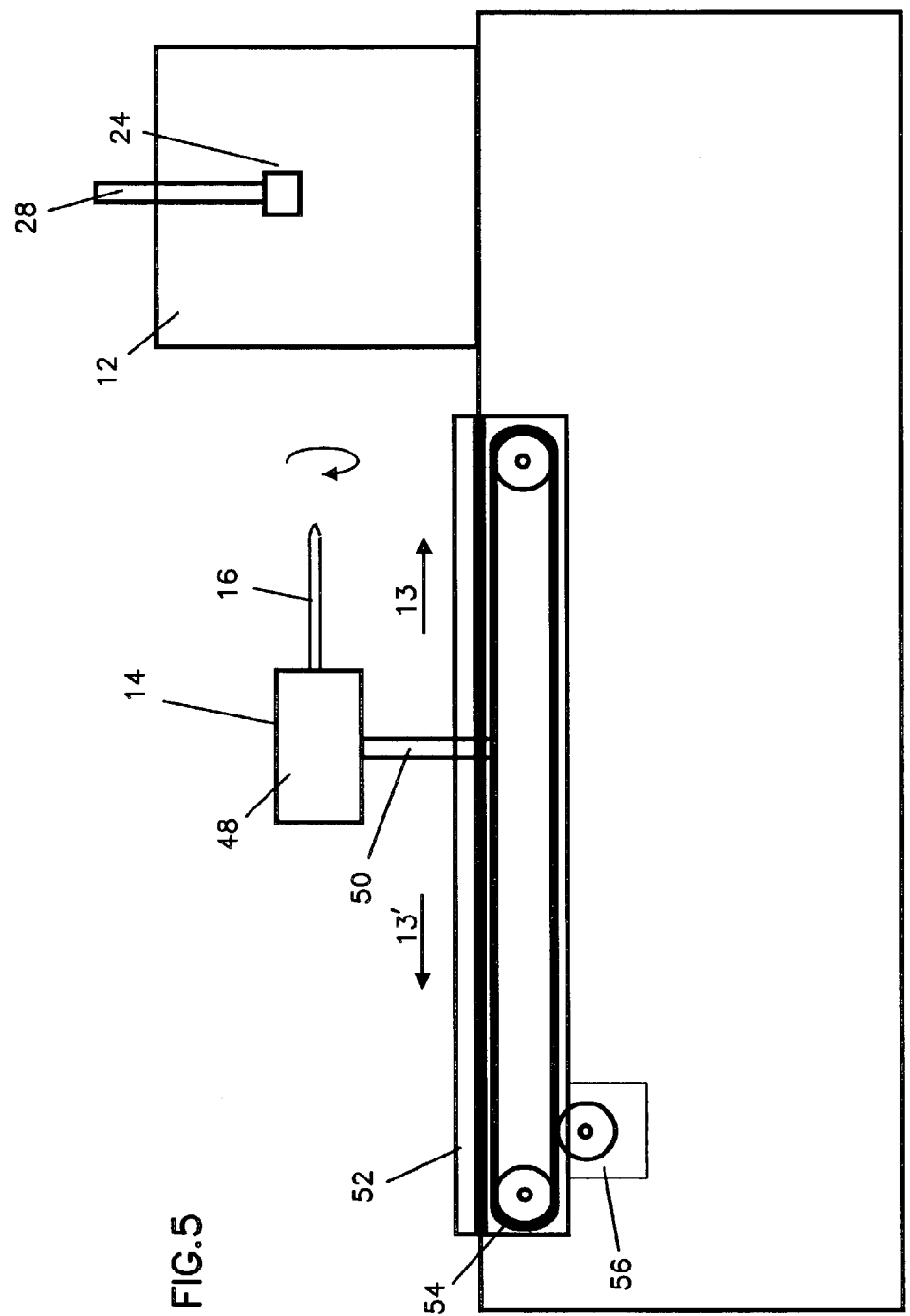
FIG. 5 illustrates a cross-sectional front view of the coating apparatus showing the device rotator and coating chamber.

Referring to FIG. 5, device rotator 14 can include device mount 16 and rotator housing 48 which can hold a motor and gearing (not shown). The rotator housing 48 is connected to neck 50 which is connected to and is slidable along the length of the track 52. Optionally, neck 50 is manually or automatically extendable and retractable to lower and raise the vertical position (height) of the device rotator 14. An adjustable neck 50 can be useful, for example, when various sized devices are coated. Track 52 directs the movement of the device rotator 14 in the direction towards, as indicated by arrow 13, or away from, as indicated by arrow 13', coating chamber 12. Device rotator 14 can be moved on the track 52 by the operation of track drive 54, which is connected to neck 50. Track motor 56 can drive the movement of the track drive 54, which can be a belt, chain, pulley, cord, or gear arrangement. The track motor 56 can be operated to move the device mount within coating chamber 12 and toward the nozzle 24 on the nozzle arm 28. The rotator housing 48 typically remains outside the coating chamber 12 during the coating steps. During the coating steps the track motor 56 can provide a back and forth movement of the device according to directions indicated by arrows 13 and 13'. Device mount 16 can be rotated by a motor within the rotator housing 48. An example of such an electric motor is the megatorque motor sold by NSK Ltd, Precision Machinery and Parts Tech Center, Gunma-Ken, Japan. The motor can operate in a clockwise or counterclockwise direction and can be controlled by a computerized processing unit (not shown).

Figure 6:
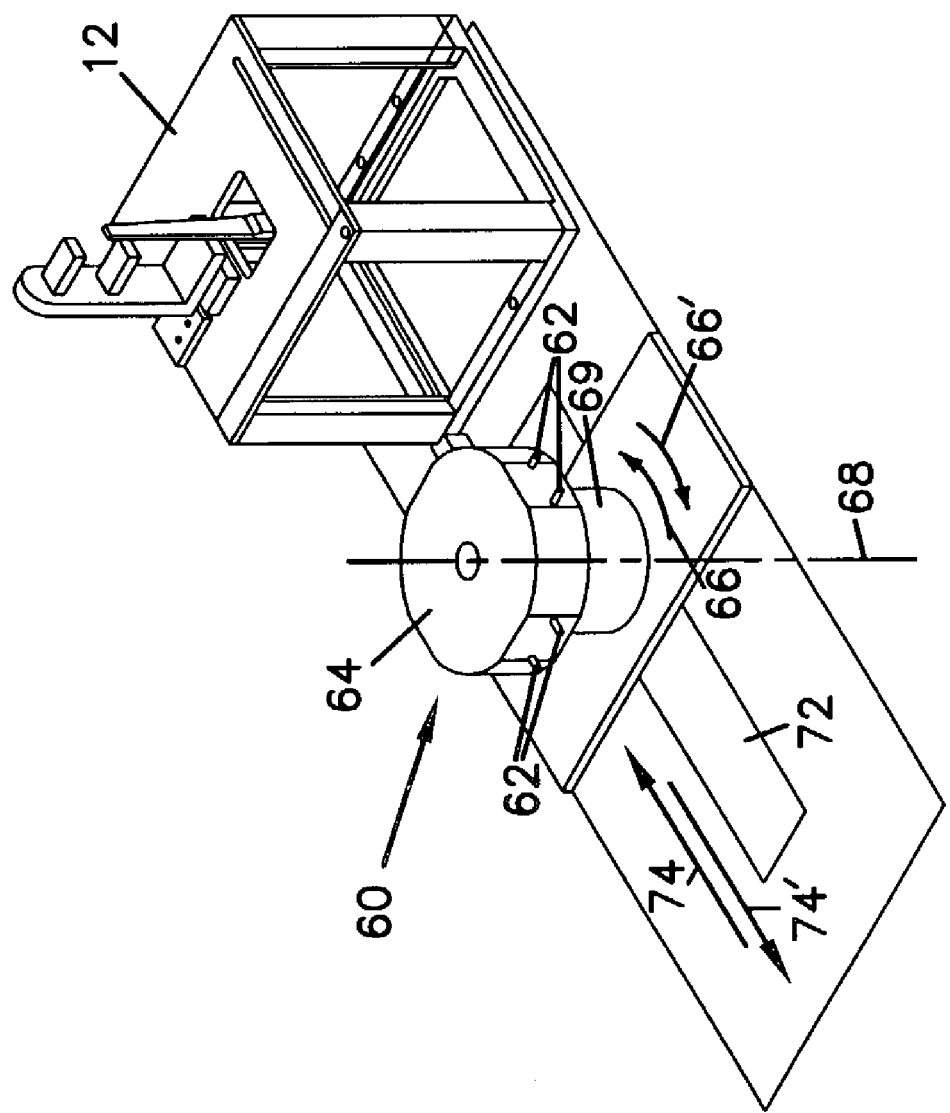
FIG. 6 illustrates an alternative embodiment of the coating apparatus having a multi-device rotator and a coating chamber.

In another embodiment, shown in FIG. 6, the coating apparatus can include a multi-device rotator 60 having a plurality of device mounts 62. Multi-device rotator 60 includes a first rotational member 64 rotatable in either direction (66 or 66') about a first axis 68. The first rotational member sits on a neck 69. Device mounts 62 are attached to the periphery of the first rotational member 64 and extend radially outward. The first rotational member 64 is rotatably driven by a motor (not shown) about the first axis 68. The first rotational member can be provided in any suitable dimensions to accommodate the desired number of devices to be coated, and arranged to provide devices to be coated in the coating chamber 12. The multi-device rotator 60 is arranged to accommodate any one of the device mounts 62 in the coating chamber 12. In many embodiments, the multi-device rotator 60 has two to eight device mounts 62 attached to the periphery of the first rotational member 64. However, the number of the device mounts attached to the periphery of the first rotational member 64 can depend on a number of factors, including, the length of the device mount 62, the size and shape of the first rotational member 64, the size of the coating chamber 12, the size of the first rotational member 64 in relation to the coating chamber 12, the size and shape of the device to be coated, etc. Therefore, in some cases more than eight device mounts can project from the multi-device rotator 60.

The multi-device rotator 60 typically includes a drive arrangement (not shown) for rotating the first rotational member 64 about the first axis 68 and for rotating the device mounts 62. The device mounts 62 may rotate about a second axis which projects radially from the first rotational member 64 in a manner perpendicular to the first axis 68. For each device mount 62 there is a second axis such that there are a plurality of second axes when there are a plurality of device mounts 62. Examples of suitable rotators and drive mechanisms can be found in U.S. patent application Ser. No. 09/657,885, commonly owned by the assignee, the disclosure of which is herein incorporated in its entirety.

The multi-device rotor 60 can be moved towards and away from the coating chamber 12 via track 72. Track 72 directs the movement of the multi-device rotator 60 in the direction towards, as indicated by arrow 74, or away from, as indicated by arrow 74', coating chamber 12. In use, the multi-device rotator 60 can provide a device to the interior of the coating chamber 12 by sliding along track 72 wherein the device enters through the device aperture 18 (not shown) in coating chamber 12. When the multi device rotor 60 is in a retracted position distal from the coating chamber 12, the first rotational member 64 can be rotated to position a device mount 62 in alignment with the device aperture 18 of the coating chamber 12. Positioning of the device mount 62 in alignment with the device aperture 18 allows the device mount 62 and attached device to be passed through the device aperture 18 when the multi-device rotator 60 is moved along track 72 towards the coating chamber 12 in direction of arrow 74. When the device and device mount 62 are inserted into the coating chamber 12, a drive mechanism can rotate the device mounts 62 thereby causing the rotation of the device in the coating chamber 62 during the coating cycle. During the coating cycle, the multi-device rotator can also move in either direction 74 or 74' to move the device along a device axis within the coating chamber. After the device has been coated, the multi-device rotator 60 can be retracted from the coating chamber 12, withdrawing the device and device mount 62 from the interior of the coating chamber 12.

In some implementations, the vertical position of the multi-device rotator 60 can be adjusted by neck 69. Neck 69 can be manually or automatically extendable and retractable to lower and raise the height of the multi-device rotator 60 and device mounts 62. An adjustable neck 69 can be useful to align a device mounted on a device mount 62 with the device aperture 18 of the coating chamber 12.

In order to coat the next device on a device mount 62 of the first rotational member 64, the first rotational member 64 can be rotated about the first axis 68 to position the next device mount 62 and attached device to be inserted into coating chamber 12 through the device aperture 18. The attached device can be positioned adjacent to the nozzle 24 of the coating unit, and the coating cycle can be performed. The device can subsequently be retracted from the coating chamber 12. This process can be repeated to coat all of the devices that are attached to the multi-device rotator 60.

The first rotational member 64 can be provided in any suitable configuration, such as a circular, square, rectangular, hexagonal, octagonal, or other configuration, to achieve the purposes herein described. In one embodiment, for example, the first rotational member 64 is provided in the form of a hexagonal rotation unit including six device mounts positioned equidistant around the periphery of the hexagonal rotation unit. However, any number of device mounts 62 can be provided on each such face or side of the rotatable member, and the number of device mounts 62 can be determined, for example, by the coating station dimensions and shape, overall dimensions of the apparatus, dimensions of each device to be coated, and the like. It is also envisioned that the multi-device rotator 60 can be arranged so that the first axis 68 is parallel with the surface of the apparatus (as compared to FIG. 6 which shows the first axis perpendicular to the surface of the apparatus). In this arrangement, the multi-device rotator 60 is rotated in a vertical plane rather than a horizontal plane (as depicted in FIG. 6).

The embodiment shown in the figures includes one device rotator movable towards and away from coating chamber. However, it is contemplated that more than one device rotator can be provided in connection with each coating chamber. The positioning and number of the device rotators can depend on the operation of the coating device. For example, two device rotators can be arranged to operate in conjunction with one coating chamber wherein each device rotator, positioned at different locations, provides devices into the coating chamber for application of a coating.

Device Mounts

Referring to FIGS. 1 and 5, the device mount 16 of the device rotator 14 is positioned to project from the device rotator 14, extending towards the coating chamber 12. The device mount 16 is typically positioned to enter the coating chamber 12 via the device aperture 18.

In another embodiment, shown in FIG. 6, device mounts 62 project radially from the first rotational member 64 of multi-rotator 60 and are rotatable about the second axes. Typically, in this embodiment, one device mount 62 of the multi-device rotator 60 is aligned with device aperture 18. Rotation of the multi-rotator 60 can allow any device mount 62 to be aligned with the device aperture 18 for insertion of the device mount 62 into the coating chamber.

Figure 7:
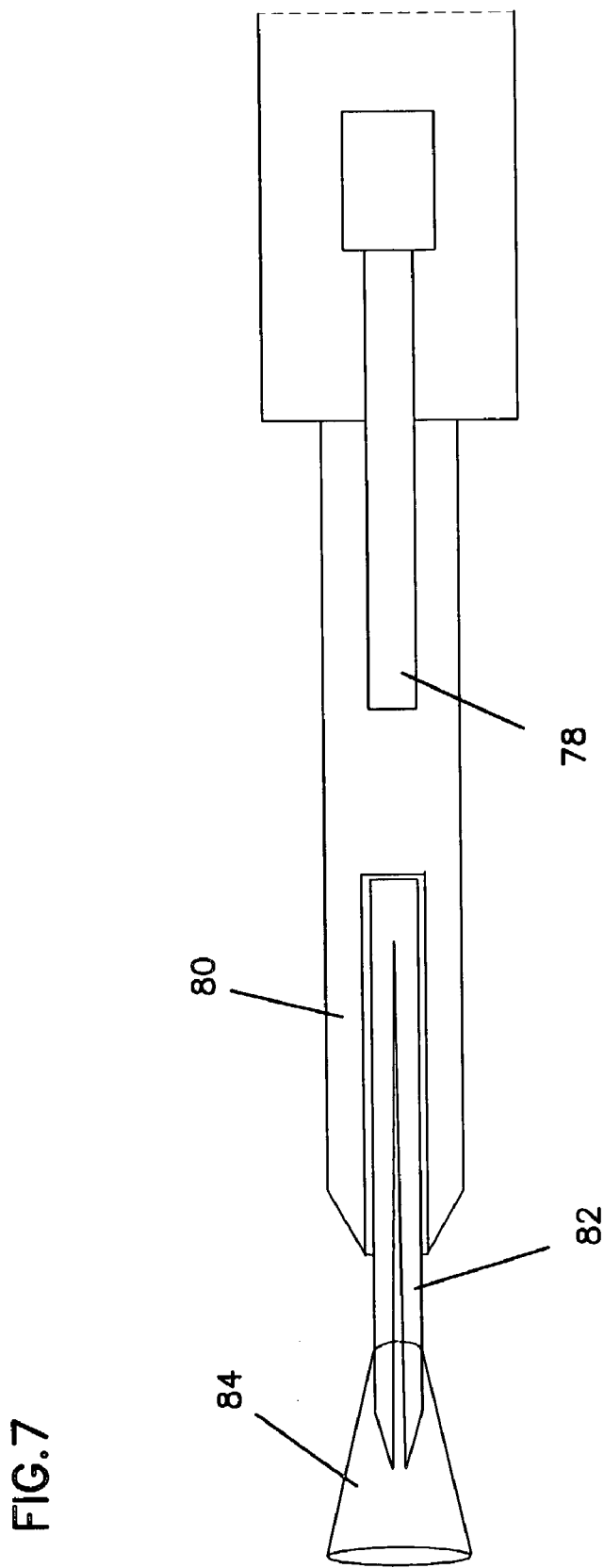
FIG. 7 illustrates a side view of an embodiment of the device mount of the invention.

Referring to FIG. 7, in one embodiment, device mounts include a gripper carrier 80 and a device gripper 82, wherein the gripper carrier 80 is separable from the device gripper 82. In another embodiment the gripper carrier 80 and a device gripper 82 are unitary. One of skill in the art, given the teachings herein, could readily modify the device to provide the gripper carrier 80 as a part of either the device rotator or the device gripper 82.

A device mount having a gripper carrier 80 and a device gripper 82 can be used as the device mount 16 on the device rotator 14 or device mount 62 on multi-device rotator 60. The design of the device mounts can be interchangeable for both device rotator 14 and multi-device rotator 60.

According to the invention, shaft 78 projects from the periphery of the device rotator 14 (not shown) and engages the gripper carrier 80. Gripper carrier 80 can include an opening (shaft 78 is shown inserted into the opening of gripper carrier 80) which can accommodate shaft 78 allowing the gripper carrier 80 to be frictionally held in place, projecting from the device rotator 14. In other embodiments, shaft 78 can have an opening into which gripper carrier 80 can be inserted. The gripper carrier 80 can be configured so that it has a standard (e.g., universally sized) opening for mounting onto the device rotator 14 or multi-device rotator 60. Additional securing of the gripper carrier 80 on the shaft 78 can be provided in the form of screws, magnets, pins, clamps, and the like. Generally, the gripper carrier 80 is removable from and remountable on the device rotator 14 or multi-device rotator 60. However, gripper carrier 80 can also be non-removably affixed to the device rotator 14 or multi-device rotator 60.

A variety of configurations can be used for the gripper carrier 80 of the invention, while still utilizing one device rotator. For example, the gripper carrier 80 can be configured to receive a medical device such as a stent, or it can be configured to receive a larger device with different dimensions. The invention can provide a device rotator that is adaptable to be used to coat any suitable device, by simply changing the gripper carriers used in connection with the device rotator.

Device gripper 82 can be provided in the form of tweezers or a different grasping and holding device. Device gripper 82 can also be specifically configured to receive a stent. Optionally, the device gripper 82 is used in connection with a collar 84 that slidably fits around the outer surface of the device gripper 82 once a device has been provided. Collar 84 thus provides a splashguard to keep the coating solution from coating and building up on the device gripper 82. Collar 84 can also provide additional stabilization of the gripper/device engagement.

The device gripper 82 can be held within a portion of the gripper carrier 80 and can be easily removed from and reinserted in the gripper carrier 80. The device gripper 82 can be held in a hollowed or grooved portion (cavity) of the gripper carrier 80 and maintained in that portion by frictional force exerted by any suitable connecting device, for example, screws, magnets, pins, clamps, or the like. The device gripper 82 may also itself have a cavity by which it attaches to the gripper carrier 80.

Device mounts 16 (or 62) are rotated at a suitable speed to achieve the desired coating uniformity, and the speed will depend upon such factors as the viscosity of the coating solution and the surface geometry of the device. Typically, the device mounts 16 (or 62) are rotated at a rate of approximately 50 rpm (revolutions per minute) to approximately 500 rpm. In some embodiments the device mounts 16 (or 62) are rotated at approximately 100 rpm. When using this embodiment of the device rotator, the solvent used for the coating solution flashes off quickly, so that uneven application of the coating onto the devices can be minimized or avoided. Various solvents can be used depending on the type of coating to be applied. Suitable solvents include tetrahydrofuran, amongst others.

Method of Coating a Device

Generally, operation of the invention is performed by attaching a device to be coated to a device mount 16 of a device rotator 14, purging the coating chamber 12 with gas to obtain a desired humidity level, delivering the device into the coating chamber 12 by moving the device rotator 14 towards the coating chamber 12 wherein the device passes through an aperture 18 and into the coating chamber 12, rotating the device mount 16 about the device axis, thereby rotating the device, moving the device back and forth in a sweeping motion, and supplying coating solution through the nozzle 24 at a sufficient rate and direction to apply a substantially uniform coating while the device is rotating about the device axis. The device to be coated in this method maybe a medical device, such as a stent.

The method, according to one implementation of the invention, includes steps of: a) providing an apparatus for coating a device, the apparatus comprising: i) a coating chamber comprising a coating unit and an atmosphere maintenance system; and ii) a device rotator having at least one device mount; b) mounting the device onto the device mount; c) purging the coating chamber to reduce humidity in the coating chamber via activation of the atmosphere maintenance system; d) maintaining a reduced humidity content in the chamber; e) inserting the device into the coating chamber; f) disposing a coating material on the device through the coating unit simultaneously with step d); g) rotating the device mounts about the device axis simultaneously with step f).

In one embodiment, as illustrated in FIG. 1, a device rotator 14 having one device mount 16 can be used for delivering the device to the coating chamber 12 and for rotation of the device during the coating cycle. In another embodiment, as illustrated in FIG. 6, a multi-device rotator 60 having a plurality of device mounts 62 having a plurality of attached devices can be used to deliver the devices into the coating chamber 12 and for rotation of the devices during the coating cycle.

In most embodiments, the device is introduced into the coating chamber 12 by the device rotator 14 which can slidably move along track 52 in the direction of the coating chamber 12. The movement of the device rotator 14 can be driven by a track drive 54 powered by a track motor 56. Operation of the track drive 54 and track motor 56 can be manual or automated and can be coordinated with the operation of aspects of the coating chamber 12, for example, the atmosphere maintenance system. In an embodiment, the introduction of the device into the coating chamber 12 is coordinated with operation of the atmosphere maintenance system. For example, when a desired level of humidity is achieved in the coating chamber 12, the track drive 54 and track motor 56 can be actuated to introduce the device into the coating chamber 12. Alternatively, the coating chamber 12 can be purged of humidity after the device has been introduced into the chamber.

The device is typically introduced into the coating chamber 12 via the device aperture 18 in the first panel 20a of the coating chamber 12. The device, attached to the device mount 16, is passed through the device aperture 18 and into the coating chamber 12 and positioned proximal to the nozzle 24 of the coating unit. Typically, at least a portion of the device is positioned in a "coating zone" which is proximal to the nozzle 24. Generally, the device is positioned beneath the nozzle 24 in the coating zone. According to the invention, the nozzle 24 can be positioned (via the positioning member 30) to provide a predetermined distance, or range of distance, between the nozzle 24 and device. The coating zone is limited to minimize waste.

The coating zone includes an area surrounding the device to be coated that is defined by the area of solution sprayed over and around the device. The coating zone is determined by such factors as the relative position of the nozzle 24, diameter of the nozzle, amount of atomization of the solution, the distance between the nozzle 24 and the device to be coated, the speed of solution delivery from the nozzle 24, and the length of the device to be coated. Optimizing the coating zone will allow one to achieve the desired coating with minimal reagent waste.

In many embodiments the invention is used in connection with spray deposition of the coating material, although other deposition methods may be used in connection with the invention.

According to the invention, and depending on the device to be coated, the distance between the device and nozzle 24 can be adjusted. This can be accomplished by adjusting the positioning member 30 to change the position of the nozzle 24 within the chamber. The position can be changed in any direction in the chamber, for example, to any coordinate along any axis X, Y, or Z. The positioning parameters are typically established by the limits of the movement of the positioning member 30. Alternatively, this can be accomplished, for example, by adjusting the neck 50 of the device rotator 14, thereby raising or lowering the device rotator 14, device mount 16, and attached device.

To purge the coating chamber 12 an inert gas is provided through a gas inlet port 38. The gas is provided at a suitable pressure and flow rate to maintain a desired humidity level in the coating chamber 12, as registered by a humidity sensor 36. The desired humidity level will depend upon the particular application. In some embodiments the humidity is maintained at about 0% in the chamber. In other embodiments the humidity may be higher such as 90% or more. For many applications the humidity is between 25% and 35%, or about 30%. The desired humidity will depend on various factors including the device, coating solution, solvent, and desired drying time. To purge the coating chamber 12 of the humidity, a high initial flow rate of gas can be used followed by a gas flow rate that is reduced and that is able to maintain relatively constant humidity conditions within the coating chamber 12. The coating chamber 12 can be purged of the water vapor with the device inserted or retracted from the coating chamber 12. The device is generally not coated until the humidity levels in the coating chamber 12 has been reduced and stabilized. If the device has been inserted into the coating chamber 12 and the coating chamber 12 is purged subsequently, it is preferable that device aperture 18 is not completely sealed by the insertion of the device and device mount 16 into the coating chamber 12. This can allow for water vapor to escape the chamber during the purging process.

Gas can be introduced into the coating chamber 12 at any time during the coating process. In some cases the flow of gas can be reduced or temporarily stopped during application of a coating to the device. This can be useful if the influx of gas from the gas inlet port 38 adversely affects the spray coating cycle. In particular this method of operation can be beneficial when the coating chamber 12 is relatively small.

When the device is inserted in the coating chamber 12 and the humidity content in the chamber is reduced to a desired level, the coating unit can be actuated to provide a coating to the device. The distance between the nozzle 24 and portions of the device is generally maintained at a constant, predetermined distance, for example, approximately 2 cm to approximately 10 cm, or about 4 cm to about 6 cm. When coating solution is supplied through the nozzle 24, the nozzle 24 forms a spray deposition pattern of a diameter approximately 0.5 to approximately 2 cm, or about 1 cm in some embodiments. The diameter of the spray deposition pattern will vary depending upon the nozzle used.

In addition to gas being provided to the coating chamber 12 via the gas inlet port 38, gas is also typically delivered in the coating chamber via the spray nozzle 24. Gas, typically an inert gas such as nitrogen, is provided along with the coating solution to the nozzle 24 for generating a spray of coating solution. Typically, the amount of gas delivered via the spray nozzle 24 is less than the amount of gas delivered via the gas inlet port 38.

The coating solution is supplied from a solution source (not shown) and driven by a pump (not shown) and through solution delivery line 26 to the nozzle 24. The device can be rotated and stationary or, can be rotated and mobile in directions (referring to FIG. 5) indicated by arrows 13 and 13' during the coating cycle. For example, the device can be moved back and forth in the spray path by moving the device rotator 14 on the track 52, driven by the track drive 54. One back and forth motion is referred herein as one "sweep". By operation of the track drive 54, the device can continue to travel along the device axis (i.e., along the direction of arrows 13 and 13') during the sweep motion. Typically, the device is rotated in the range of 50–500 revolutions/minute and moved horizontally back and forth in the range of 5–20 sweeps/minute. The track drive 54 can be operated at a predetermined speed to provide a uniform coating to the desired portions of the device.

The delivery rate of the solution through the nozzle 24 can be about 5 µl per second to about 30 µl per second, or about 10 µl to about 20 µl per second when the viscosity of the solution is about 1 centipoise (cp). The delivery rate refers to the rate at which the coating solution is supplied through the nozzle 24. The delivery rate of the coating solution can be adjusted depending upon such factors as the viscosity of the coating solution, and the solvent system used with the coating solution. For example, when a solvent such as tetrahydrofuran (THF) is used, which flashes off devices quickly, the delivery rate can be increased, whereas when a solvent such as water is used, a slower delivery rate is typically used.

Delivery of the solution is typically performed by operation of the solution pump for a predetermined period of time. One delivery unit of the solution is herein referred to as a "shot". According to the amount of solution to be delivered to the device, the pump can be operated for longer or shorter periods of time. In the time the pump is activated and delivering a spray of the solution to the device, the device is rotating and can be moving back and forth along the device axis in the spray path. Multiple shots can be applied to the device as desired, and the number of shots applied to the device is adjusted to achieve the desired coating weight.

The volume of coating solution applied for each shot can be precisely adjusted depending upon such factors as the solvent system used and the viscosity of the coating solution. Typically, for a coating solution using THF as a solvent, the coating solution is applied in approximately 50 µl to approximately 70 µl shots, in many embodiments, approximately 50 μl to approximately 65 μl shots. For this shot volume, typically three shots will be applied to the device in one coating application.

The coating unit can be adjusted so that there is a delay between shots of the coating solution onto the device. The delay between shots, or pulse, provides a method to apply the coating solution adequately. The length of delay between shots depends upon such factors as the shot volume and the length of time required to dry the coating solution before applying additional coating solution. Typically, a delay of approximately 2 seconds to approximately 10 seconds, or about 4 seconds to about 6 seconds is used for a shot volume of approximately 65 μl, when the coating solution comprises a THF solvent system.

The above parameters are exemplary only and can be precisely adjusted to achieve the desired coating thickness and characteristics desired, while minimizing waste of the coating solution. Also, a program control can be provided to allow required adjustments and monitoring of conditions of coating to achieve desired coating thickness.

In order to provide a desired surface coating, a gas can be provided through gas delivery channel 34 to the nozzle 24 (FIG. 4) simultaneously with the delivery of coating solution. A gas is supplied from a gas source (which can be the same gas source used to provide gas to the atmosphere maintenance system; not shown) to nozzle 24 to atomize the coating solution to shear the solution for application on the device surface. In an embodiment, the gas is an inert gas, such as nitrogen. The gas is provided at suitable pressure, for example from 70.3 to 3515.3 g/cm$^2$ (or 1 to 50 psi), to sufficiently atomize the solution on the surface of the device. The rate of delivery of the solution is adjusted to provide a suitable thickness of coating on the surface of the device, for example, 1–50 μm. Gas can be supplied through the nozzle before and after providing the solution through the nozzle. Supply of the coating solution, and gas if desired, is generally started before the device reaches the coating zone, so that the nozzle is purged to rid the nozzle of any unwanted debris or dried coating solution. This can allow cleaning of the nozzle prior to solution application. The nozzle 24 can also be brought in contact with a cleaning solution or other solution to remove any residual coating solution from the nozzle and to prevent dehydration of the nozzle.

After the coating solution is applied, the solution delivery can be shut off to avoid waste of the materials. The coated device can remain in the coating chamber 12 for a period of time in reduced humidity conditions for drying. When desired, the device can be moved out of the coating zone and retracted from the coating chamber 12 via the device aperture 18.

When the device rotator 14 has moved on track 52 away from the coating station 12 and the device has been retracted from the interior of the coating station 12, a next device can be attached to the device mount 16 for application of a coating. In one embodiment, the device can be removed from device mount 16, for example, by removal of the device gripper from the gripper holder, then a next device can be mounted on the device mount for coating. Optionally, the device mount 16 and device are removed from the shaft 78 of device rotator 14 and a next device mount 16 and device are attached. In another embodiment, multi-device rotator 60 is moved on track away from the coating station 12, retracting the device from the interior of the coating station 12. When the device mount 62 and device are sufficiently spaced from the coating chamber 12, the multi-device rotator 60 rotates freely about the vertical axis to advance the next device mount to a position for introduction of the next device and device mount into the coating chamber 12. The steps of retraction, rotation, and introduction, of the multi-device rotator are repeated stepwise until all devices are properly coated.

In some cases, when coating a device, for example, a stent, only the portion of the stent projecting radially from the device gripper 82 will be coated. In these cases, when it is desired to coat the entire surface of the device, the devices are removed from the device rotator by an operator, inverted, and remounted on the device mount so that the other half of the device (the uncoated portion of the device) is projected radially from the device rotator and is thereby coated. The coating operation is repeated for the second half of the device.

The duration of a coating cycle will depend upon various factors, including the number of devices loaded onto the multi-device rotator 60 and the type of coating solution applied to the device. The distance separating the device mounts 62 can be adjusted depending upon the geometry of the devices to be coated, the speed of the coating cycle, the coating solution, and the like. Additionally, the use of any drying or curing steps will affect the duration of a coating cycle. The duration of a coating cycle can be of any time but typically is in the range of at least 10 seconds to 5 minutes.

As a result of the arrangement and rotation of components, the invention provides a combination of advantages such as efficiency, reduction of human factors in the coating operation, and uniform coating of device. The invention provides an improved apparatus and method for coating medical devices, particularly medical devices having surface geometries that are otherwise difficult to uniformly coat. A large number of devices can be coated, and a plurality of coating layers can be applied to each device, in a relatively short period of time.

The following example helps to illustrate an embodiment of the present invention but is only exemplary and therefore will be understood to not limit the scope of the invention as claimed.

EXAMPLE 1

Coating Cardiovascular Stents

A method of the invention was performed by way of the example as follows. Cardiovascular stents of length approximately 18 mm were inserted into device grippers and a collar was slid over the juncture between the device gripper and stent. The device gripper, stent and collar were then inserted into a cavity formed in the gripper carrier. The device gripper was inserted into the gripper carrier and pushed until the device gripper seated into the chamber of the gripper carrier and was frictionally held in place. The gripper carrier was then mounted onto the shaft of the device mount of the device rotator. Nitrogen was introduced into the humidity chamber prior to introduction of the stent on the device mount to maintain approximately 10% relative humidity.

Once the stent was mounted onto the device rotator and positioned as shown in FIG. 1, a coating cycle was started. The device rotator was moved towards the coating chamber in the direction of arrow 13 (as shown in FIG. 5) to insert the stent in the coating chamber and underneath the nozzle 24 of the coating unit.

During the coating of the stent, the humidity was maintained at 10% or less. A 5 mg/ml coating solution comprising 33.3% by weight drug (dexamethasone), and 66.7% by weight poly(ethylene-co-vinyl acetate) (PEVA) in THF was provided through the solution delivery line from a solution source to the nozzle. During the coating operation, the device rotator was moved in directions parallel to the axis of the device mount, shown as the direction of arrows 13 and 13' in FIG. 5. One half of one back and forth movement, or one sweep, covered a horizontal distance of 12 mm, which was performed in approximately 5 seconds. Simultaneously with the application of the coating, the device mounts were rotated at a constant rate about radial axes at a speed of 100 rpm to allow uniform application of the coating.

The coating solution pump was adjusted to provide a solution delivery rate of 20 µl per second to the stent surface. One shot of coating solution lasted 7 seconds and during that time the stent traveled back and forth 1–2 times (1–2 sweeps) in the spray path. A delay of five (5) seconds was provided between each coating shot. A total of 7 shots of coating solution was required to achieve the desired coating thickness.

The distance from the nozzle to the stent was adjusted to minimize waste of the coating solution and provide a coating to the surface of the stent. The distance from nozzle to stent was 3.5 cm. Nitrogen, $N_2$, was provided at a rate of 421.8 g/cm$^2$ (6 psi).

Once sufficient coating solution was applied, the solution pump was shut off and the device rotator was shutoff. The stent was removed from the device rotator, which had retracted to its original position outside the coating chamber. The application deposited approximately 140 micrograms of coating on the stent. Once a coating application was performed, the device gripper was removed from the device mount and the coated stent was replaced with an uncoated stent mounted on a device gripper. The coating application was repeated to coat the second half of the stents. Stents were removed and weighed to determine the amount coating deposited.

The invention has been described with reference to various specific embodiments and techniques. However, it will be apparent to one of ordinary skill in the art that many variations and modifications may be made while remaining within the spirit and scope of the invention. While the invention has been described in relation to coating stents, one of skill in the art would readily appreciate the applicability of the invention to a variety of devices.

All publications and patent applications in this specification are herein incorporated by reference to the same extent as if each individual publication or patent application was specifically and individually incorporated by reference.

We claim:

1. An apparatus for coating a medical device, the apparatus comprising:
   a. a coating chamber comprising
      a mounting panel; and
      a plurality of removable panels;
      wherein the mounting panel defines a plurality of slots, wherein the removable panels fit in the slots:
   b. a device rotator having at least one device mount; and
   c. an atmosphere maintenance system;
   wherein the atmosphere maintenance system modulates gaseous conditions inside the coating chamber;
   wherein the atmosphere maintenance system comprises a humidity sensor.

2. The apparatus according to claim 1, wherein the device rotator is movable via a track mechanism.

3. The apparatus according to claim 1, wherein the atmosphere maintenance system lowers humidity in the coating chamber and maintains lowered humidity conditions therein.

4. The apparatus according to claim 3, wherein the atmosphere maintenance system lowers humidity in the coating chamber to between 0 and 90 percent relative humidity and maintains lowered humidity conditions therein.

5. The apparatus according to claim 4, wherein the atmosphere maintenance system lowers humidity in the coating chamber to between 0 and 40 percent relative humidity and maintains lowered humidity conditions therein.

6. The apparatus according to claim 3, wherein the atmosphere maintenance system comprises a gas inlet port.

7. The apparatus according to claim 1, wherein the coating chamber comprises at least one coating unit, wherein the coating unit further comprises a nozzle.

8. The apparatus according to claim 7, wherein the nozzle is adjacent to the device mount when the device mount is inserted into the coating chamber.

9. The apparatus according to claim 8, wherein the nozzle is above the device mount when the device mount is inserted into the coating chamber.

10. The apparatus according to claim 7, wherein the coating unit further comprises a gas delivery line and a solution delivery line.

11. The apparatus according to claim 10, wherein the solution delivery line delivers between 1 µl per second and 50 µl per second of coating solution to the nozzle.

12. The apparatus according to claim 1, wherein the coating chamber comprises at least one panel having a device aperture allowing passage of the device into the coating chamber.

13. The apparatus according to claim 1 wherein the coating chamber has a volume of less than 2000 cubic inches.

14. The apparatus according to claim 13 wherein the volume of the coating chamber is between 200 and 2000 cubic inches.

15. The apparatus according to claim 1 wherein the device rotator comprises:
   a device rotation axis,
   wherein the device mount is rotatable around the device rotation axis.

16. The apparatus according to claim 15 wherein the coating provided by the apparatus to the medical device is uniform about the device rotation axis.

17. The apparatus according to claim 15 wherein the device mount rotates about the device rotation axis at between 10 and 500 rotations per minute.

18. The apparatus according to claim 1 wherein the device rotator comprises:
   a first rotational portion rotatable about a first axis;
   a plurality of device mounts positioned on the first rotational portion that extend radially outward from the first axis,
   a plurality of secondary axes that extend radially outward from the first rotational portion in the plane of the device mounts such that the secondary axes are perpendicular to the first axis;
   wherein the device mounts are rotatable about the secondary axes;
   wherein the first rotational portion rotates to align device mounts with the coating chamber.

19. The apparatus according to claim 1 wherein the device mount comprises a device gripper and a gripper carrier.

20. An apparatus for coating a device, the apparatus comprising:
- a. a coating chamber comprising
    - i) at least one coating unit having at least one nozzle; and
    - ii) an atmosphere maintenance system comprising a gas inlet port and a humidity sensor, wherein the distance between the humidity sensor and the nozzle is less than the distance between the humidity sensor and the gas inlet port.
- b. a device rotator having at least one device mount; wherein the apparatus allows insertion and retraction of the device on the device mount into and out of the coating chamber.

* * * * *